United States Patent [19]
Nestor, Jr. et al.

[11] Patent Number: 5,783,179
[45] Date of Patent: Jul. 21, 1998

[54] C-REACTIVE PROTEIN FRAGMENT WITH IMMUNOMODULATORY ACTIVITY

[75] Inventors: John J. Nestor, Jr., Cupertino; Teresa H. Ho, Los Altos; Deborah A. Eppstein, Palo Alto; Philip L. Felgner, San Diego, all of Calif.; Barbara P. Barna, Berea; Sharad D. Deodhar, Shaker Heights, both of Ohio

[73] Assignee: Syntex (U.S.A.) Inc., Palo Alto, Calif.

[21] Appl. No.: 743,613

[22] Filed: Aug. 9, 1991

[51] Int. Cl.[6] .................. A61K 45/05; A61K 38/04; C07K 5/00
[52] U.S. Cl. ..................... 424/85.2; 530/327; 514/14
[58] Field of Search ........................... 530/327, 328; 424/85.2

[56] References Cited

U.S. PATENT DOCUMENTS

| | | | |
|---|---|---|---|
| 4,859,765 | 8/1989 | Nestor, Jr. et al. | 530/333 |
| 5,003,065 | 3/1991 | Merritt et al. | 540/469 |

FOREIGN PATENT DOCUMENTS

| | | |
|---|---|---|
| 8905151 | 6/1989 | WIPO . |
| WO 89/05151 | 6/1989 | WIPO . |

OTHER PUBLICATIONS

Robey, et al. *J. Biol. Chem.* pp. 7053–7057, 1987.
Deodar et al *J. FASEB* v. 3 A 831, 1989.
Barna et al, *Fed Proc* v. 46 (3) 762, 1987.
*J. of Biological Chem.* (1986), pp. 7053–7057, F. A. Robey, et al. Proteolysis of Human C-reactive Protein Produces Peptides with Potent Immunomodulating Activity.

*J. of Immunology* (1990), vol. 145, No. 5, pp. 1469–1476, E. G. Shephard, et al. Peptides Generated from C-reactive Protein by a Neutrophil Membrane Protease.

*Cancer Research* (1982), vol. 42, pp. 5084–5088, S. D. Deodhar, et al. Inhibition of Lung Metastases in Mice Bearing a Malignant Fibrosarcoma by Treatment with Liposomes Containing Human C-reactive Protein.

*J. Leukocyte Biology* (1990), Supplemental 1:53, B. Barna, et al. Modulation of Pulmonary Macrophage Concentration by a Synthetic of C-reactive Protein (CRP) Peptide.

*FASEB J.*, (1989), 3:A831, S. Deodar, et al. Enhanced Anti-Tumor Effect by Combination Therapy with Human C-Reactive Protein (CRP) Peptide and IL2 in C57 Mice Bearing the Fibrosarcoma T241.

*Fed. Proc.*, (1987), 46 (3):762, B. Barna, et al. Macrophage Activation by a Synthetic Peptide of Human C-Reactive Protein (CRP). (Meeting Abstract).

*Primary Examiner*—Cecilia J. Tsang
*Assistant Examiner*—S. Marshall
*Attorney, Agent, or Firm*—Heller Ehrman White & McAuliffe

[57] ABSTRACT

Compounds having immunomodulatory activity comprising the optionally modified dodecapeptide fragment A-(SEQ ID No: 1)-B corresponding to residues 174 to 185 of C-reactive protein (CRP), pharmaceutical compositions thereof, and methods of treating cancer with the compositions. Liposomal formulations containing the CRP-peptide fragment are particularly efficacious when administered in conjunction with interleukin-2.

15 Claims, 1 Drawing Sheet

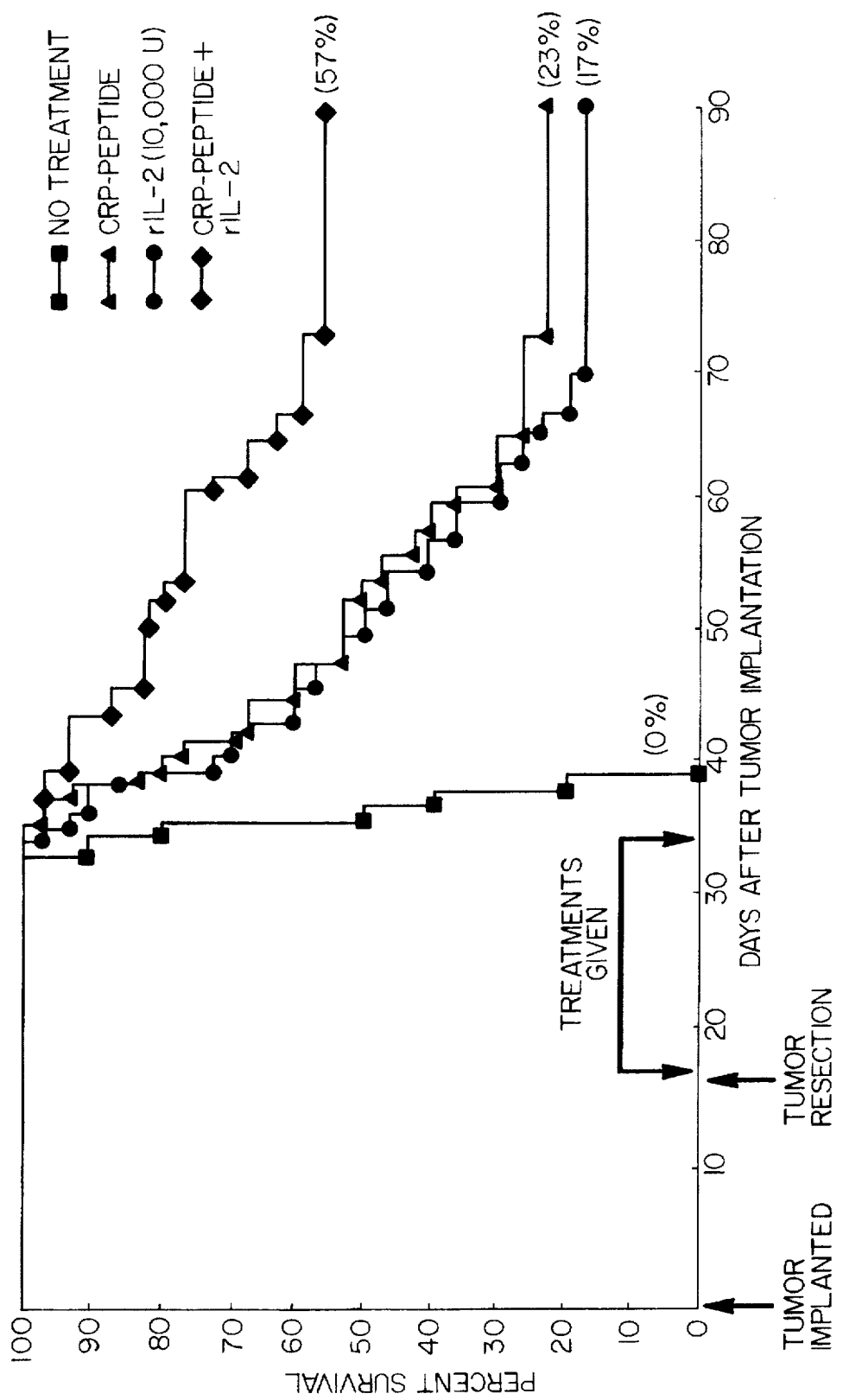

C-REACTIVE PROTEIN FRAGMENT WITH IMMUNOMODULATORY ACTIVITY

BACKGROUND OF THE INVENTION

1. Field of the Invention

This invention relates to pharmaceutical compounds exhibiting immunomodulatory activity, methods of preparation of such compounds and their use in the treatment of cancer.

2. Description of Related Art

C-reactive protein (CRP) is an acute phase serum protein, the secretion from the liver of which is increased up to 1000 fold in response to tissue injury, infection, or inflammation. J. J. Morley and I. Kushner, *Ann. N.Y. Acad. Sci.*, 389, 406 (1982). The disclosure of this and all other patents and publications mentioned in this application are incorporated herein by reference. Although the precise physiological function for CRP has not been elucidated in detail, it is thought to play a role in opsonization, inflammation, and possibly immunomodulation. J. M. Kilpatrick and J. E. Volanakis, *J. Immunol.*, 134, 3364 (1985). It has also been suggested that CRP may be enzymatically cleaved into peptide fragments related to the putative immunomodulatory peptide tuftsin. F. A. Robey, K. Ohura, S. Futaki, N.Fujii, H. Yajima, N. Goldman, K. D. Jones, and S. Wahl, *J. Biol. Chem.* 262, 7053 (1987). These peptides were suggested to have a suppressive effect on inflammation and immune function. E. G. Shepard, R. Anderson, O Rosen, M. S. Myer, M. Fridlein, A. F. Strachan and F. C. DeBeer *J. Immunology* 145, 1469 (1990).

Native CRP encapsulated in liposomes has been shown to be taken up by phagocytic cells, and to exert immunomodulatory affects on macrophage tumoricidal activity and oxidative metabolism. B. P. Barna, S. D. Deodhar, S. Gautam, B. Yen-Lieberman and D. Roberts, *Cancer Res.*, 44, 305 (1984). Treatment of tumor-bearing animals with CRP liposomes inhibited metastasis and promoted survival. S. D. Deodhar, K. James, T. Chiang, M. Edinger, and B. P. Barna, *Cancer Res.*, 42, 5084 (1982).

We have shown that a dodecapeptide fragment of CRP in liposomes has the same beneficial effect in tumor-bearing animals as the native protein. B. P. Barna, P. Felgner, S. D. Deodhar, T. L. Ho, J. J. Nestor, *Fed. Proc.* 46, 762 (1987). Furthermore, this peptide sequence is unrelated to any fragment previously considered to be active.

SUMMARY OF THE INVENTION

The compound of this invention is an optionally modified dodecapeptide A-(SEQ ID No:1)-B, A-Ile-Tyr-Leu-Gly-Gly-Pro-Phe-Ser-Pro-Asn-Val-Leu-B, wherein A is an acyl group or H, and B is OH or $NR_2$, with each R independently H, $C_1$–$C_6$ alkyl, $C_1$–$C_6$ haloalkyl, or $C_1$–$C_6$ aralkyl.

In one embodiment, the invention comprises the encapsulation of this peptide in a liposomal or other formulation. The invention also relates to the use of this peptide in conjunction with cytokines, especially interleukin-2 (IL-2).

This dodecapeptide and its formulations are useful for the treatment of cancer and infectious diseases.

The invention further comprises a solid state method for preparing a compound of the invention and pharmaceutically acceptable salts thereof via sequential condensation of protected amino acids, removal of protecting groups and, optionally, covalently bound solid support, from the protected polypeptide to afford the compound.

BRIEF DESCRIPTION OF THE DRAWING

The Figure displays the results of survival studies in mice treated with CRP-peptide.

DETAILED DESCRIPTION OF THE INVENTION

Abbreviations and Definitions

The abbreviations for the various common amino acids are as recommended by the IUPAC-IUB Commission on Biochemical Nomenclature, *Biochem. J.* 219:345 (1984). All peptide sequences mentioned herein are written according to the generally accepted convention in which the N-terminal amino acid is on the left and the C-terminal amino acid is on the right.

The abbreviations herein represent L-amino acids unless otherwise designated as D- or D,L-. Certain amino acids, both natural or non-natural, are achiral, e.g. glycine.

As used herein, the term "pharmaceutically acceptable salts" refers to salts that retain the desired biological activity of the parent compound without toxic side effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid and the like; (b) base addition salts formed with polyvalent metal cations such as zinc, calcium, bismuth, barium, magnesium, aluminum, copper, cobalt, nickel, cadmium, and the like; or with an organic cation formed from N,N'-dibenzylethylenediamine or ethylenediamine; or (c) combinations, of (a) and (b), e.g., a zinc tannate salt and the like.

"Acyl" refers to the organic radical derived from an organic acid by the removal of the hydroxyl group. Generally, the acyl is attached to a terminal amino acid residue on the amine nitrogen. "N-Ac" refers specifically to the N-acetyl protecting group, i.e., an acetyl group attached to a terminal amino acid residue on the amine nitrogen.

The term "$C_1$–$C_6$ alkyl" refers to a straight, branched chain, or cyclic hydrocarbon radical having from 1 to 6 carbon atoms, such as methyl, ethyl, n-propyl, isopropyl, n-butyl, isobutyl, sec-butyl, t-butyl, n-pentyl, n-hexyl, cyclopentyl, cyclohexyl and the remaining branched and cyclic 5 or 6 carbon radicals.

The term "$C_1$–$C_6$ haloalkyl" refers to an alkyl group as defined above in which one or more hydrogen atoms is replaced by a halogen, such as —$CF_3$, —$CH_2CF_3$, and the like. Halogens include fluorine, chlorine, bromine, and iodine, preferably fluorine.

The term "$C_1$–$C_6$ aralkyl" refers to an alkyl group as defined above in which one or more hydrogen atoms is replaced by an aryl group, preferably a phenyl group. Aralkyl includes aromatic groups such as benzyl or phenethyl.

The term "CRP-peptide (SEQ ID NO:1)" is used to describe the dodecapeptide fragment corresponding to residues 174 to 185 of C-reactive protein or a blocked form thereof, A-(SEQ ID No:1)-B. A blocked form of the CRP-peptide(SEQ ID No:1) is one in which the N-terminus, the C-terminus or both are provided with end groups which improve the specificity, stability, or delivery properties of the peptide. In the sequence as defined by A-(SEQ ID No:1)-B, A, which is H in the unblocked peptide, may be an acyl group, preferably N-Ac, and B, OH in the unblocked peptide, may be $NR_2$, NHR, or $NH_2$, where R is selected from $C_1$–$C_6$ alkyls, $C_1$–$C_6$ haloalkyls, and $C_1$–$C_6$ aralkyls.

SYNTHESIS OF THE PEPTIDES

The CRP-peptide (SEQ ID NO: 1) of the instant invention may be synthesized by various techniques such as those in J. M. Stewart and J. D. Young, *Solid Phase Peptide Synthesis* 2nd edit. Pierce Chemical Co., Rockford, Ill., 1984, and J. Meienhofer, *Hormonal Proteins and Peptides*, Vol. 2, p. 46., Academic Press (New York), 1973 for solid phase peptide synthesis and E. Schroder and K. Lubke, *The Peptides*, Vol. 1, Academic Press (New York), 1965 for classical solution synthesis.

In general, these methods involve the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary amino or carboxyl group and any reactive side chains suitably protected, under conditions suitable for forming the amide linkage. After all the desired amino acids have been linked in the proper sequence, any remaining protecting groups (and any solid support) are removed to afford the crude form of the polypeptide.

Finally the peptide is desalted and purified chromatographically to yield the final product.

Alternatively, the CRP-peptide ( SEQ ID No: 1) may be prepared by fermentation or recombinant techniques.

A preferred method of preparing the CRP-peptide (SEQ ID No 1) involves solid phase peptide synthesis. In this method the α-amino ($N^\alpha$) function of each amino acid is protected by an acid-or base-sensitive group. The protecting groups should be stable to the conditions of peptide linkage formation, while being readily removable without destruction of the growing peptide chain or racemization of any of the chiral centers contained therein. Suitable α-amino protecting groups include, but are not limited to, t-butoxycarbonyl (Boc), benzyloxycarbonyl (Cbz), o-chlorobenzyloxycarbonyl (Cl-Z), biphenylisopropyloxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butoxycarbonyl, 9-fluorenylmethoxycarbonyl (Fmoc) and the like, especially t-butoxycarbonyl (Boc). Suitable side chain protecting groups include, but are not limited to, for tyrosine: benzyl (Bzl), o-bromobenzyloxycarbonyl, 2,6-dichlorobenzyl, isopropyl, cyclohexyl, cyclopentyl and acetyl; for serine: t-butyl, t-butyldimethylsilyl, trimethylsilyl, pivalyl, trityl, benzyl and tetrahydropyran-2-yl.

The C-terminal amino acid is attached to a suitable solid support. Suitable solid supports useful for the above synthesis are those materials which are inert to the reagents and reaction conditions of the stepwise condensation-deprotection reactions, as well as being insoluble in the media used. Examples of commercially available resins include styrene/divinylbenzene resins modified with a reactive group, e.g., chloromethylated styrene/ldivinylbenzene copolymer, hydroxymethylated styrene/divinylbenzene copolymer, and the like. Merrifield resin (1% crosslinked chloromethylated styrene/divinylbenzene copolymer) is preferred. When the C-terminus of the compound is an amide, i.e. B is $NR_2$, a particularly useful support is the p-methylbenzhydrylamino-polystyrene-divinylbenzene polymer described by Rivaille, et al, *Helv. Chim. Acta.*, 54:2772 (1971).

Attachment to the chloromethylated styrene/divinylbenzene resin may be accomplished by the reaction of the $N^\alpha$-protected amino acid, especially the Boc-amino acid, as its cesium, tetramethylammonium, triethylammonium, 1,5-diazabicyclo-[5.4.0]undec-5-ene, or similar salt in ethanol, acetonitrile, N,N-dimethylformamide (DMF), and the like, especially the cesium salt in DMF, with the chloromethylated resin at an elevated temperature, for example between about 40° and 60° C., preferably about 50° C., for from about 12 to 72 hours, preferably about 48 hours.

The $N^\alpha$-Boc-amino acid may be attached to the benzhydrylamine resin, for example, by means of an N,N'-diisopropylcarbodiimide (DIC)/1-hydroxybenzotriazole (HBt) mediated coupling for from about 2 to about 24 hours, preferably about 2 hours at a temperature of between about 10° and 50° C., preferably 25° C. in a solvent such as dichloromethane or DMF, preferably dichloromethane.

The successive coupling of protected amino acids may be carried out by methods well known in the art, typically in an automatic peptide synthesizer. Following neutralization with triethylamine or similar base, each protected amino acid is preferably introduced in approximately 1.5 to 2.5 fold molar excess and the coupling carried out in an inert, nonaqueous, polar solvent such as dichloromethane, DMF, or mixtures thereof, preferably in dichloromethane at about ambient temperature. Representative coupling agents are N,N'-dicyclohexylcarbodiimide (DCC), N,N'-diisopropylcarbodiimide (DIC) or other carbodiimide either alone or in the presence of 1-hydroxybenzotriazole (HBt), O-acyl ureas, benzotriazol-1-yl-oxy-tris-(pyrrolidino) phosphonium hexafluorophosphate (PyBop), N-hydroxysuccinimide, other N-hydroxyimides or oximes. Alternatively, protected amino acid active esters (e.g. p-nitrophenyl, pentafluorophenyl and the like) or symmetrical anhydrides may be used.

At the end of the solid phase synthesis the fully protected peptide is removed from the resin. When the linkage to the resin support is of the benzyl ester type, cleavage is by means of aminolysis with an alkylamine or fluoroalkylamine for peptides with a alkylamide C-terminus, or by aminolysis with, for example, ammonia/methanol or ammonia/ethanol for peptides with an unsubstituted amide C-terminus at a temperature between about −10° and 50° C., preferably about 25° C., for between about 12 and 24 hours, preferably about 18 hours. Peptides with a free —COOH carboxy-terminus (C-terminus) may be obtained by HF or other strongly acidic deprotection regime, or by saponification. Alternatively, the peptide may be removed from the resin by transesterification, e.g., with methanol, followed by aminolysis or saponification. The protected peptide may be purified at this point by silica gel chromatography.

The removal of the side chain protecting groups from the peptide is performed by treating the aminolysis product with, for example, anhydrous liquid hydrogen fluoride in the presence of anisole or other carbonium scavenger, treatment with hydrogen fluoride/pyridine complex, treatment with tris(trifluoroacetyl)boron and trifluoroacetic acid, by reduction with hydrogen and palladium on carbon or polyvinylpyrrolidone, or by reduction with sodium in liquid ammonia, preferably with liquid hydrogen fluoride and anisole at a temperature between about −10° and +10° C., preferably about 0° C., for between about 15 minutes and 2 hours, preferably about 1 hour.

For peptides on the benzhydrylamine resin, the resin cleavage and deprotection steps may be combined in a single step utilizing, liquid hydrogen fluoride and anisole as described above.

The solution is desalted (e.g. with BioRad AG-3 anion exchange resin) and the peptide purified by a sequence of chromatographic steps employing any or all of the following types: ion exchange on a weakly basic resin in the acetate form; hydrophobic adsorption chromatography on underivatized polystyrenedivinylbenzene (for example Amberlite® XAD); silica gel adsorption chromatography; ion exchange chromatography on carboxymethylcellulose; partition chromatography (e.g. on Sephadex G-25); countercurrent distribution; or high performance liquid chromatography (HPLC), especially reversed-phase HPLC on octyl- or octadecylsilylsilica bonded phase column packing.

Thus, another aspect of the present invention relates to a method for preparing CRP-peptides and pharmaceutically acceptable salts thereof comprising sequentially condensing protected amino acids, removing protecting groups and, optionally, covalently bound solid support to afford a compound as defined in the Sequence Listing as SEQ ID No:1 or a blocked form thereof.

ADMINISTRATION

In the practice of this invention an effective amount of a CRP-peptide (SEQ IQ No:1) or a pharmaceutical composition containing same is administered to the subject. These compounds or compositions may be administered by any of a variety of routes depending upon the specific end use, including orally, parenterally (including subcutaneous, intramuscular and intravenous administration), rectally, buccally (including sublingually), transdermally or intranasally. The most suitable route in any given case will depend upon the use and the subject involved. The compound or composition may also be administered by controlled-release, e.g., from monolithic or reservoir-type microcapsules, vesicles, micelles, or liposomes or via depot implant. A preferred method of administration is parenterally in a liposomal formulation.

In general for the uses as described in the instant invention, it is expedient to administer the active ingredient in amounts between about 3 and 10000 µg/kg body weight, most preferably from about 10 to about 100 µg/kg body weight. For human therapy, the active ingredient will be administered preferably in the range of from about 10 to about 100 µg/kg/day. This administration may be accomplished by a single administration, by distribution over several applications or by controlled release in order to achieve the most effective results.

The exact dose and regimen for administration of these compounds and compositions will necessarily be dependent upon the needs of the individual subject being treated, the type of treatment, and the degree of affliction. In general, parenteral administration requires lower dosage than other methods of administration which are more dependent upon absorption.

A further aspect of the present invention relates to pharmaceutical compositions comprising as an active ingredient a CRP-peptide of the present invention in admixture with a pharmaceutically acceptable, non-toxic carrier. As mentioned above, such compositions may be prepared for use for parenteral (subcutaneous, intramuscular or intravenous) administration, particularly in the form of liquid solutions or suspensions; for oral or buccal administration particularly in the form of tablets or capsules; for intranasal administration, particularly in the form of powders, nasal drops or aerosols; and for rectal or transdermal administration.

The compositions may conveniently be administered in unit dosage form and may be prepared by any of the methods well-known in the pharmaceutical art, for example as described in *Remington's Pharmaceutical Sciences*, 17th edition, Mack Publishing Company, Easton, PA., 1985. Formulations for parenteral administration may contain as common excipients sterile water or saline, alkylene glycols such as propylene glycol, polyalkylene glycols such as polyethylene glycol, oils of vegetable origin, hydrogenated naphthalenes and the like. For oral administration, the formulation can be enhanced by the addition of bile salts and also by the addition of acylcarnitines (*Am. J. Physiol.* 251:332 (1986)). Formulations for nasal administration may be solid and contain as excipients, for example, lactose or dextran, or may be aqueous or oily solutions for administration in the form of nasal drops or metered spray. For buccal administration typical excipients include sugars, calcium stearate, magnesium stearate, pregelatinated starch, and the like.

When formulated for nasal administration the absorption across the nasal mucous membrane is enhanced by surfactant acids, such as for example, glycocholic acid, cholic acid, taurocholic acid, ethocholic acid, desoxycholic acid, chenodesoxycholic acid, dehydrocholic acid, glycodeoxycholic acid, cyclodextrins and the like. See, B. H.Vickery, "LHRH and Its Analogs-Contraception and Therapeutic Applications", Pt. 2, B. H. Vickery and J. J. Nestor, Eds., MTP Press, Lancaster, UK, 1987.

One or more surfactant acids or salts, but preferably a single pharmaceutically acceptable acid salt, can be added to the compounds of the instant invention, if desired, for nasal, rectal, buccal, oral or transdermal administration. Suitable pharmaceutically acceptable surfactant salts are those salts which enhance peptide absorption, as well as the compound's surfactant characteristics, and which are not deleterious to the subject or otherwise contraindicated. Such salts are for example those salts derived from inorganic bases which include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, trimethamine, dicyclohexylamine, choline and caffeine.

The amount of surfactant used for the practice of this invention will be an amount effective to increase the absorption of the CRP peptide (SEQ ID No:1). Such an amount is often in the range between 0.2 and 15 percent, more often 0.2 to 5 percent by weight/volume of the solution. It is preferred that the surfactant be present in an amount between about 0.5 to 4 percent by weight/volume, most preferably about 2 percent by weight/volume.

It may be desirable to deliver the compounds of the present invention to the subject over prolonged periods of time, for example, for periods of one week to one year from a single administration. Various slow release, monolithic or reservoir-type microcapsules, depot implant systems or injectable dosage forms may be utilized.

For example, a dosage form may contain a pharmaceutically acceptable non-toxic salt of the compound which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzylethylenediamine or ethylenediamine; or (c) combinations of (a) and (b) e.g. a zinc tannate salt.

Additionally, the compounds of the present invention or, preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like.

Another type of slow release depot formulation for injection or implantation would contain the compound or salt dispersed or encapsulated in a slowly degrading, non-toxic, non-antigenic polymer such as a polylactic acid/polyglycolic acid polymer. See, for example, Kent, et al., U.S. Pat. No. 4,675,189. The compounds or, preferably, relatively insoluble salts such as those described above may also be formulated in cholesterol or other lipid matrix pellets, or silastomer matrix implants. Additional slow release, depot implant or injectable formulations, e.g. liposomes, are well known in the literature. See, for example, *Sustained and Controlled Release Drug Delivery Systems*, J. R. Robinson ed., Marcel Dekker, Inc., New York, 1978.

A preferred formulation for delivery of the CRP-peptide (SEQ ID No:1) is in liposomes. Liposomes are microscopic vesicles consisting of concentric lipid bilayers. Structurally, liposomes range in size and shape from long tubes to spheres, with dimensions from a few hundred Angstroms to fractions of a millimeter. Regardless of the overall shape, the bilayers are generally organized as closed concentric lamellae, with an aqueous layer separating each lamella from its neighbor. Vesicle size normally falls in a range of between about 20 and about 30,000 nm in diameter. The liquid film between lamellae is usually between about 3 and 10 nm.

A variety of methods for preparing liposomes have been described in the literature. For specific reviews and information on liposome formulations, reference is made to reviews by Pagano and Weinstein (*Ann. Rev. Biophys. Bioeng.*, 7, 435–68 (1978)) and Szoka and Papahadjopoulos (*Ann. Rev. Biophys. Bioeng.*, 9, 467–508 (1980)) and additionally to U.S. Pat. Nos. 4,229,360; 4,224,179; 4,241,046; 4,078,052; and 4,235,871, the disclosures of which are incorporated by reference herein.

Typically, liposomes can be divided into three categories based on their overall size and the nature of the lamellar structure. The three classifications, as developed by the New York Academy Sciences Meeting, "Liposomes and Their Use in Biology and Medicine," of December, 1977, are multi-lamellar vesicles (MLV's), small uni-lamellar vesicles (SUV's) and large uni-lamellar vesicles (LUV's).

SUV's range in diameter from approximately 20 to 50 nm and consist of a single lipid bilayer surrounding an aqueous compartment. Unilamellar vesicles can also be prepared in sizes from about 50 nm to 600 nm in diameter. While unilamellar vesicles are of fairly uniform size, MLV's vary greatly in size up to 10,000 nm, or therabouts, are multi-compartmental and contain more than one bilayer. LUV liposomes are so named because of their large diameters which range from about 600 nm to 30,000 nm; they can contain more than one bilayer.

Liposomes may be prepared by a number of methods, not all of which can produce the three different types of liposomes. For example, ultrasonic dispersion by means of immersing a metal probe directly into a suspension of MLV's is a common way for preparing SUV's.

Preparing liposomes of the MLV class usually involves dissolving the lipids in an appropriate organic solvent and then removing the solvent under a gas or air stream. This leaves behind a thin film of dry lipid on the surface of the container. An aqueous solution is then introduced into the container with shaking in order to free lipid material from the sides of the container. This process disperses the lipid, causing it to form into lipid aggregates or liposomes.

Liposomes of the LUV variety may be made by slow hydration of a thin layer of lipid with distilled water or an aqueous solution of some sort.

Alternatively, liposomes may be prepared by lyophilization. This process comprises drying a solution of lipids to a film under a stream of nitrogen. This film is then dissolved in a volatile, freezable, organic solvent, e.g., cyclohexane or t-butanol, frozen, and placed on a lyophilization apparatus to remove the solvent. To prepare a pharmaceutical formulation containing a water-soluble drug, an aqueous solution of the drug is added to the lyophilized lipids, whereupon liposomes are formed.

Lipophilic drugs may be incorporated into the bilayer by dissolving them with the lipid in the organic phase and then removing the organic phase. Hydration with the aqueous phase will result in the incorporation of the lipophilic drug into the liposomal bilayer structure. This applies both to lyophilization and thin film methods. The ratio of drug to lipid may be up to about 20% by weight, preferably from about 0.001% to about 0.1%.

UTILITY AND ASSAY PROCEDURES

The compounds of this invention are surprisingly active in view of their small size and unique structure. The CRP-peptide was assayed for activity in the mouse T241 fibrosarcoma model, whereby the ability to block lung metastasis formation is measured.

The utility of the compound of this invention is in the treatment of cancer, particularly metastatic cancer of the lung and liver and infectious disease, particularly systemic fungal infections. In these conditions, immune stimulation is known to have a beneficial effect and the usefulness of this peptide formulated by itself or in conjunction with cytokines can be inferred from the animal model described above.

Cytokines are nonantibody proteins, such as lymphokines, released by certain cell populations on contact with specific antigens and which act as intercellular mediators, as in the generation of immune response.

Lymphokines are soluble substances released by sensitized lymphocytes on contact with specific antigens, which help effect cellular immunity by stimulating activity of monocytes and macrophages; these include, but are not limited to, chemotactic, mitogenic (blastogenic), migration-inhibitory, and transfer factors, lymphotoxin, and interleukin-2.

The lymphokine may be incorporated into the delivery system containing the CRP-peptide, may be separately encapsulated, or may be delivered in suspension or solution. The composition may further optionally contain a cytostatic or cytotoxic drug.

In a preferred embodiment, liposomes containing the CRP-peptide (SEQ ID No:1) are administered in a therapeutic regimen which also includes the intraperitoneal administration of interleukin-2.

PREPARATION A

Boc-Leu-O-Resin

Boc-Leu-OH*$H_2O$ (6.0 g, 26 mmol) was dissolved in 50 mL of ethanol and 10 mL of $H_2O$. The solution was adjusted to pH 7.0 by addition of a 1.5M solution of cesium carbonate. The mixture was evaporated to dryness and further dried by evaporation of solutions in absolute EtOH (repeated 3 times). The cesium salt was dried under vacuum overnight and used without further purification. The cesium salt was dissolved in 200 ml DMF. To the DMF solution, 1% chloromethylated styrene-divinylbenzene resin (15.4 g, 1.3 meq/g, 20 mmol) was added and the suspension was agitated at 50° C. for 48 hours. The resin was filtered and washed successively with DMF, a DMF/$H_2O$ mixture (4:1), DMF, $CH_2Cl_2$, EtOH, $CH_2Cl_2$ and dried in vacuo. Amino acid analysis of the resin showed 0.974 meq/g uptake.

EXAMPLE 1

H—Ile—Tyr—Leu—Gly—Gly—Pro—Phe—Ser—Pro—Asn—Val—Leu—OH (SEQ ID No. 1)

In the reaction vessel of a Beckman 990 peptide synthesizer was placed 1.02 g (1.0 mmol) of Boc-Leu-O-resin; protected amino acids were sequentially added to the resin by means of a standard synthesis program, as taught for example in U.S. Pat. Nos. 4,234,571, 4,667,014, 4,801,577 and others. The resin was coupled sequentially with a 2.0 to 5.0 fold, preferably 2.0 to 2.5 fold, molar excess of each protected amino acid and N,N'-diisopropylcarbodiimide (DIC). The resin was treated during successive coupling cycles with:

| | |
|---|---|
| 0.54 g | Boc-Val-OH, |
| 0.58 g | Boc-Asn-OH and HBt (0.34 g), |
| 0.54 g | Boc-Pro-OH, |
| 0.38 g | Boc-Ser (Bzl)-OH, |
| 0.66 g | Boc-Phe-OH, |
| 0.54 g | Boc-Pro-OH, |
| 0.44 g | Boc-Gly-OH, |
| 0.44 g | Boc-Gly-OH, |
| 0.62 g | Boc-Leu-OH · $H_2O$ |
| 0.87 g | Boc-Tyr (2,6-dichlorobenzyl)-OH, |
| 0.60 g | Boc-Ile-OH · $H_2O$ |

The protected peptide resin was removed from the reaction vessel, filtered and dried in vacuo to yield the protected intermediate. A 2.1 g batch of the peptide resin was deprotected and the peptide removed from the resin by treatment with 20 mL of anhydrous liquid HF in the presence of 2 mL of anisole (scavenger) in a Kel-F reaction vessel at 0° C. for 1 hour. The HF was evaporated under vacuum and the residue of H-Ile-Tyr-Leu-Gly-Gly-Pro-Phe-Ser-Pro-Asn-Val-OH, SEQ ID No:1 as its HF salt, was washed with ether (2×20 mL) and dissolved in $H_2O$ (2×25 mL). Lyophilization of the aqueous solution gave the crude product as a white powder.

The crude peptide was purified by preparative high performance liquid chromatography on RP 18 packing material (2.5×100 cm; 15 micron) using an appropriate gradient of $CH_3CN$ in aqueous $NH_4OAc$ (0.03M, pH=4.5). The fractions were cut for purity rather than yield (UV monitor) and purity assessed by analytical HPLC on Vydec analytical columns (5 micron packing). The pooled fractions were lyophilized to yield pure (>95%) H-Ile-Tyr-Leu-Gly-Gly-Pro-Phe-Ser-Pro-Asn-Val-Leu-OH SEQ ID No:1 as a white powder of $[\alpha]^{25}_D$–68. 1°(C 0.4, HOAc)

EXAMPLE 2

Preparation of Liposomes

Multilamellar large-vesicle liposomes were prepared from phosphatidylcholine and phosphatidylserine (Avanti Biochemicals, Inc. Pelham, Ala.) using a 1:1 molar ratio. Twenty-five mL of an aqueous CRP-peptide solution containing the CRP-peptide SEQ ID No:1 of Example 1 (27 µg/mL) was vortexed for 1 min in a nitrogen-filled tube containing 250 µmol of the phospholipids as a dry film. The newly formed liposomes were centrifuged (30 min. at 20,000 ×g) in a refrigerated ultracentrifuge Beckman Model LF-75 (Beckman Instrument Co., Fullerton, Calif.) and washed to remove any free CRP peptide SEQ ID No:1. The pelleted liposomes were then resuspended in calcium- and magnesium-free Hanks' balanced salt solution at a concentration of 2.5 µmol lipid per 0.1 mL for injection by the orbital sinus route. Under these condition the encapsulation ratio was 4 µL aqueous phase per µmol of phospholipid, as determined by labeling of CRP-peptide by the technique of Bolton and Hunter, Biochem J. 133:529–539 (1977). Thus, the total amount per animal per injection was 0.25 µg of CRP-peptide per 1.75 mg (2.5 µmol) of liposome lipid in 0.1 mL.

EXAMPLE 3

Tumor Implantation and Evaluation of Lung Metastases

The procedures have been described in detail previously (Deodhar, et al, Cancer Res 42:5084–5088, 1982). Suspensions of 5×10⁵ viable T241 fibrosarcoma cells in 0.1 ml of Hanks's balanced salt solution were injected subcutaneously into the dorsum of one hind foot of ten male C57BL/6 mice (Jackson Laboratories, Bar Harbor, Me.) per experiment. Seventeen days after tumor implantation, the tumor-bearing foot was amputated below the knee. The mean tumor weight at this stage was 152 ±58 (S.E.M.) mg. The tumor weight was determined by subtracting the weight of an amputated normal foot from that of a tumor-bearing foot. Previous studies have shown that T241 fibrosarcoma starts seeding the lung parenchyma by Day 10 after foot tumor implantation; by Day 17, virtually all animals have lung macro- and/or micrometastases. The animals were then randomized into control and experimental groups, and appropriate therapy was started after amputation of the tumor-bearing foot.

Treatments consisted of intravenous (orbital sinus) injections of liposomes containing CRP, liposomal CRP-peptide of Example 2, or liposomal CRP-peptide of Example 2 plus intraperitoneal injections of non-encapsulated soluble recombinant interleukin-2 (Cetus Corp., Emeryville, Calif.), or non-encapsulated interleukin-2 (IL-2) alone, whereas the control groups received either no treatment, liposomes containing buffer medium alone, or liposomes containing buffer medium plus non-encapsulated CRP peptide. Each experimental or control group consisted of at least 10 mice. A total of 6 liposome injections was given; each consisted of 2.5 μmol of lipid containing 0.25 μg peptide suspended in 0.1 mL of saline, given on alternate days (3 injections per week for 2 weeks). IL-2 was injected daily intraperitoneally, for 5 consecutive days, followed by 2 days rest, again for 5 consecutive days, followed by 2 days rest, and then for a final 2 days (for a total of 12 treatments over a 16-day period). On Day 35 of the experiment, all animals were killed, and the lungs were evaluated for number and size of metastases.

Tumor metastases could be clearly recognized as raised, hemorrhagic, opaque, and dense nodules, distinguishable from the smooth, glistening, spongy, and pink normal lung parenchyma. The metastatic foci were also confirmed microscopically in doubtful cases. To obtain an approximate assessment of the total metastatic tumor burden in the lungs, the "metastatic index", reflecting both number and size of metastases, was calculated as follows. Each metastasis less than 0.5 mm in diameter was graded as I, between 0.5 and 1 mm in diameter as Grade II, between 1.0 and 2 mm diameter as Grade III, and >2 mm diameter as Grade IV. All the grade scores were then added to determine the metastatic index for a given animal, and the mean index was then calculated for a given control or experimental group of animals. For example, an animal with 4 lung metastases with one of each grade (I, II, III, and IV) would be considered to have a metastatic index of 10 (ie, 1×1+1×2+1×3+1×4). Group results were compared in terms of both mean metastatic index and the median number of metastases per mouse using the Mann-Whitney test. The results are shown in Table 1, wherein the efficacy of CRP-peptide in MLV is shown to be equivalent to that of native CRP in MLV.

TABLE 1

EFFICACY OF LIPOSOME-ENCAPSULATED CRP-PEPTIDE

| Treatment | No. Animals with Lung Metastases | Metastatic Index (+ SEM) | No. of Metastatic Foci (+ SEM) |
|---|---|---|---|
| None | 10/10 | 70.3 ± 14.1 | 18.9 ± 3.3 |
| Buffer MLV[a] | 10/10 | 74.2 ± 5.7 | 20.2 ± 1.7 |
| Native CRP in MLV[a] | 7/10 | 16.5 ± 4.8* | 5.7 ± 1.5* |

TABLE 1-continued

EFFICACY OF LIPOSOME-ENCAPSULATED CRP-PEPTIDE

| Treatment | No. Animals with Lung Metastases | Metastatic Index (+ SEM) | No. of Metastatic Foci (+ SEM) |
|---|---|---|---|
| CRP-Peptide in MLV[a] | 8/10 | 18.4 ± 5.7* | 5.9 ± 1.9* |
| Buffer MLV[a] + Soluble CRP Peptide[b] | 10/10 | 64.4 ± 10.1 | 17.6 ± 2.9 |
| Soluble CRP-peptide[c] | 10/10 | 49.7 ± 10.1 | 12.9 ± 2.9 |

*p < .01 compared to buffer MLV (liposome). SEM = standard error of the mean.
[a]MLV treatments consisted of 2.5 μmols lipid in MLV containing either buffer only, or 0.25 μg CRP or CRP-peptide, i.v. 3x per week for 2 weeks.
[b]Soluble CRP-peptide (1.25 μg per dose) was administered one hour after administration of 2.5 μmoles of Buffer MLV.
[c]Soluble CRP-peptide (1.25 μg per dose) was administered alone.

EXAMPLE 4

Survival Studies with T241 Fibrosarcoma

The experimental protocol for these studies was similar to that of Example 3, with the exception that animals were observed over a period of 90 days following tumor implantation. Animals dying during that period were examined for lung metastases. At Day 90, all the surviving animals were killed and then examined for lung metastases.

Animals were treated following removal of primary tumors 17 days after tumor implantation. The results are shown in FIG. 1. Treatments consisted of: 1) No treatment; 2) MLV containing synthetic CRP peptide (SEQ ID No:1) (2.5 μmoles lipid containing 0.25 μg peptide, i.v. 3 times per week for 2 weeks); 3) soluble rIL-2 (10,000 U i.p. 5 consecutive times per week for 16 days for a total of 12 injections); and 4) regimens 2 and 3 together. Data represent percentage survival for groups of 30 animals at 90 days. CRP-Peptide MLV+rIL-2 vs all other groups, p=0.0001. CRP-peptide MLV vs control, p=0.0001 (Logrank Test).

Within 40 days, all of the untreated controls (Group 1) were dead, while 23% and 17% of those treated with regimens 2 and 3, respectively, survived through the 90-day period of the experiment. The group treated with the composite regimen 4 exhibited a 57% survival rate through the 90-day period.

What is claimed is:

1. A polypeptide having the amino acid sequence A-(SEQ ID NO: 1)-B, A-Ile-Tyr-Leu-Gly-Gly-Pro-Phe-Ser-Pro-Asn-Val-Leu-B, wherein A is H or an acyl group and B is OH or $NR_2$, each R independently selected from H, $C_1$-$C_6$ alkyl, $C_1$-$C_6$ haloalkyl, and $C_1$-$C_6$ aralkyl.

2. A polypeptide of claim 1 in which A is H and B is OH, $NR_2$ or $NH_2$.

3. A polypeptide of claim 1 in which A is acyl and B is OH, $NR_2$, or $NH_2$.

4. A polypeptide of claim 3 in which A is acetyl and B is OH, $NR_2$, or $NH_2$.

5. A polypeptide of claim 4 in which A is acetyl and B is $NH_2$.

6. A pharmaceutical composition for treating cancer in mammals comprising an effective amount of a polypeptide of claim 1 in admixture with a pharmaceutically acceptable carrier.

7. A composition of claim 6 further comprising a cytokine.

8. A composition of claim 7 in which the cytokine is a lymphokine.

9. A composition of claim 8 in which the lymphokine is interleukin-2.

10. A controlled release pharmaceutical composition for treating cancer in mammals comprising an effective amount of a polypeptide of claim 1 wherein said polypeptide is released over a period of time.

11. A controlled release composition of claim 10 wherein the polypeptide is microencapsulated.

12. A composition of claim 11 in which the polypeptide is encapsulated in liposomes.

13. A composition of claim 12 further comprising encapsulated interleukin-2.

14. A composition of claim 13 further comprising a cytotoxic or cytostatic drug.

15. A unit dosage form comprising a single therapeutically effective dose of a compound of claim 1, for treating cancer in mammals.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i i ) HYPOTHETICAL: NO ( v ) FRAGMENT TYPE: internal (xi) SEQUENCE DESCRIPTION: SEQ ID NO:1:

```
Ile Tyr Leu Gly Gly Pro Phe Ser Pro Asn Val Leu
 1           5                   10
```